United States Patent
Badin et al.

[11] Patent Number: 5,653,971
[45] Date of Patent: Aug. 5, 1997

[54] SHAVING AID COMPOSITE WITH AN INCLUSION COMPLEX OF A SKIN-SOOTHING AGENT AND A CYCLODEXTRIN

[75] Inventors: Frank E. Badin, Scituate, Mass.; Thilivali T. Ndou, Gaithersburg; Lee K. Lim, Bethesda, both of Md.; Yuling Yin, Quincy; Mingchih Michael Tseng, Hingham, both of Mass.

[73] Assignee: The Gillette Company, Boston, Mass.

[21] Appl. No.: 496,860

[22] Filed: Jun. 30, 1995

[51] Int. Cl.$^6$ ............................................. A61K 7/15
[52] U.S. Cl. ...................................... 424/73; 30/41
[58] Field of Search ........................... 424/73; 30/41

[56] References Cited

U.S. PATENT DOCUMENTS

| | | | |
|---|---|---|---|
| 4,267,166 | 5/1981 | Yajima | 424/48 |
| 4,356,115 | 10/1982 | Shibanai et al. | 252/522 A |
| 4,678,598 | 7/1987 | Ogino et al. | 252/174.17 |
| 4,789,559 | 12/1988 | Hirao et al. | 426/658 |
| 5,095,619 | 3/1992 | Davis et al. | 30/41 |
| 5,165,943 | 11/1992 | Patel et al. | 426/3 |

FOREIGN PATENT DOCUMENTS

WO88/08304  11/1988  WIPO.

OTHER PUBLICATIONS

Koczka et al, Chem. Abstracts 117:118519p (1992).

Koch, "Stabilization and Controlled Release of Perfume in Detergents", I. Int. Symp. on Cyclodextrins, pp. 487–496 (Budapest, 1981).

Primary Examiner—Thurman K. Page
Assistant Examiner—James M. Spear
Attorney, Agent, or Firm—Stephan P. Williams

[57] ABSTRACT

The present invention is directed to a shaving system of the wet shave type comprising a blade member (one or more) and a structure which supports or holds the blade member and which has an external skin engaging portion in proximity to the blade member. The skin engaging portion includes an improved shaving aid composite (or lubricating strip) which contains an inclusion complex of a skin-soothing agent, such as menthol, with a cyclodextrin. Preferably the shaving aid composite comprises a matrix of a water-insoluble polymer, an effective amount of a skin lubricating water-soluble polymer dispersed within the matrix, and an inclusion complex of a skin-soothing agent with a cyclodextrin. Alternatively, the shaving aid composite may comprise a sheath of water-insoluble polymer that surrounds a core which includes a skin-lubricating water-soluble polymer and an inclusion complex of a skin-soothing agent with a cyclodextrin. The improved shaving aid composite is capable of retaining during normal storage conditions substantially all of the skin-soothing agent included during fabrication of the composite and delivering an effective amount of the skin-soothing agent during use.

19 Claims, 1 Drawing Sheet

SHAVING AID COMPOSITE WITH AN INCLUSION COMPLEX OF A SKIN-SOOTHING AGENT AND A CYCLODEXTRIN

BACKGROUND OF THE INVENTION

The present invention relates to a shaving system of the wet shave type, more particularly to a shaving system with an improved shaving aid composite.

It is now well known that shaving comfort can be enhanced by affixing to a razor cartridge a shaving aid composite, also known as a lubricating strip, which continuously releases a shaving aid, typically a lubricant, during the shaving process. See, for example, U.S. Pat. No. 4,170,821 and GB 2,024,082. The shaving aid composite generally comprises a water-insoluble polymer matrix, typically polystyrene, and a water-soluble shaving aid, typically polyethylene oxide, which leaches out of the composite during shaving to enhance shave comfort.

Unfortunately, conventional shaving aid composites suffer from the disadvantage that they release an insufficient amount of the shaving aid, particularly after the first three or four shaves where release of the shaving aid may drop off to negligible quantities. Accordingly, recent efforts have been made to improve shaving aid composites so as to enhance and prolong release of the shaving aid. Such efforts have resulted in improved shaving aid composites which include the following: incorporation of low molecular weight release enhancing agent, such as polyethylene glycol, into the matrix, disclosed in U.S. Pat. No. 5,113,585; the use of ethylene vinyl acetate copolymer as the matrix material, disclosed in U.S. Pat. No. 5,349,750; incorporation of a water-swellable polymer such as Salsorb 84, a cross-linked polyacrylic, disclosed in (U.S. Ser. No. 08/121,153); incorporation of a compatibilizer material such as polyethylene oxide-polypropylene oxide copolymer (e.g. Poloxamer 182), disclosed in U.S. Pat. No. 5,454,164; filed Mar. 17, 1994 and co-extrusion of a core comprising a water-leachable shaving aid within a sheath of water-insoluble polymer, wherein the sheath has a plurality of openings to facilitate release of the shaving aid, disclosed in (U.S. Ser. No. 08/332,293 now abandoned). All of the aforementioned patents or patent applications are incorporated herein by reference.

It has also been suggested in U.S. Pat. No. 5,095,619 that a water-insoluble essential oil, such as menthol, may be advantageously included in a shaving aid composite. However, it has been found in practice that a substantial amount of the essential oil is lost due to volatilization prior to use, rendering the composite unable to deliver an effective amount of the essential oil. It is an object of the present invention to provide a shaving aid composite (i.e. lubricating strip) which is capable of retaining during normal storage conditions substantially all of a skin-soothing agent, such as an essential oil or cooling agent, included during fabrication of the composite and delivering an effective amount of the skin-soothing agent during use.

SUMMARY OF THE INVENTION

The present invention is directed to a shaving system of the wet shave type comprising a blade member (one or more) and a structure which supports or holds the blade member and which has an external skin engaging portion in proximity to the blade member. The shaving system may be a disposable shaving cartridge adapted for coupling to and uncoupling from a razor handle or it may be a shaving head which is integral with a razor handle so that the complete razor is discarded as a unit when the blade or blades become dulled. The blade edge cooperates with the skin engaging portion to define shaving geometry.

The skin engaging portion includes an improved shaving aid composite which comprises an inclusion complex of a skin-soothing agent with a cyclodextrin. Preferably the shaving aid composite comprises a matrix of a water-insoluble polymer and, dispersed within the matrix, a skin lubricating water-soluble polymer and an inclusion complex of a skin-soothing agent with a cyclodextrin. Alternatively, the shaving aid composite may comprise a sheath of water-insoluble polymer that surrounds a core which includes a skin-lubricating water-soluble polymer and an inclusion complex of a skin-soothing agent with a cyclodextrin. The improved shaving aid composite (or lubricating strip) is capable of retaining during normal storage conditions substantially all of the skin-soothing agent included during fabrication of the composite and delivering an effective amount of the skin-soothing agent during use.

DETAILED DESCRIPTION OF THE INVENTION

Figure 1:
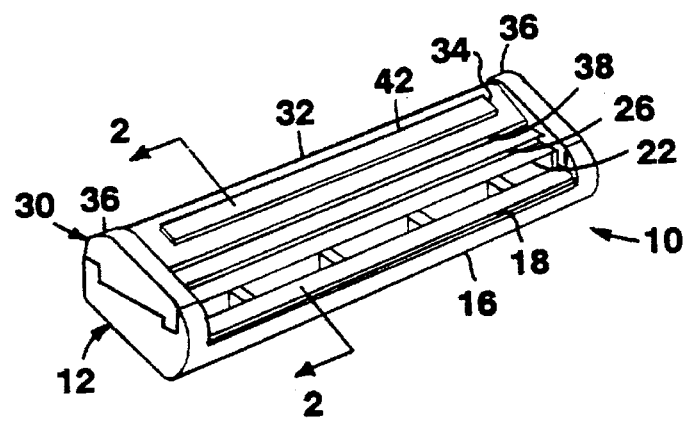
FIG. 1 is a perspective view of a razor unit in accordance with the invention.
Figure 2:
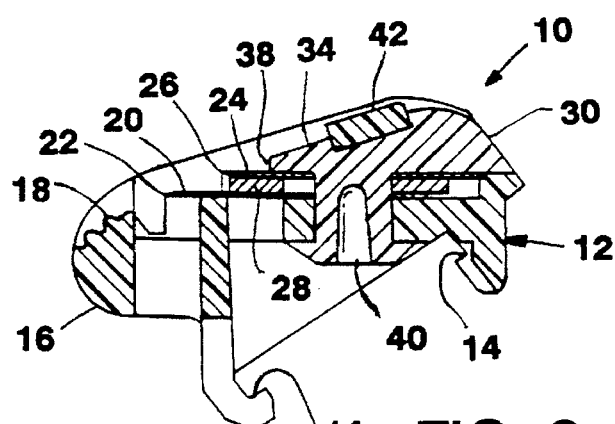
FIG. 2 is a sectional view taken along the line 2—2 of FIG. 1.

The shaving unit 10 shown in FIGS. 1 and 2 includes base or platform member 12 molded of high impact polystyrene that includes integral coupling groove structure 14 for attachment to a razor handle and guard structure 16 that defines a transversely extending forward skin engaging surface 18. On the upper surface of platform 12 are disposed steel leading blade 20 having a sharpened edge 22, steel following blade 24 having sharpened edge 26, and aluminum spacer member 28 that maintains blades 20 and 24 in spaced relation. Cap member 30 is molded of high impact polystyrene and has body portion 32 that defines skin engaging surface 34 that extends transversely between forwardly projecting end walls 36 and has a front edge 38 that is disposed rearwardly of blade edge 26. Integral rivet portions 40 extend downwardly from transversely extending body portion 32 and pass through holes in blades 20 and 24, spacer 28, and platform 12 to secure cap 30, blades 20, 24 and spacer 28 on platform 12. Adhesively affixed to skin engaging surface 34 is shaving aid composite 42.

Figure 3:
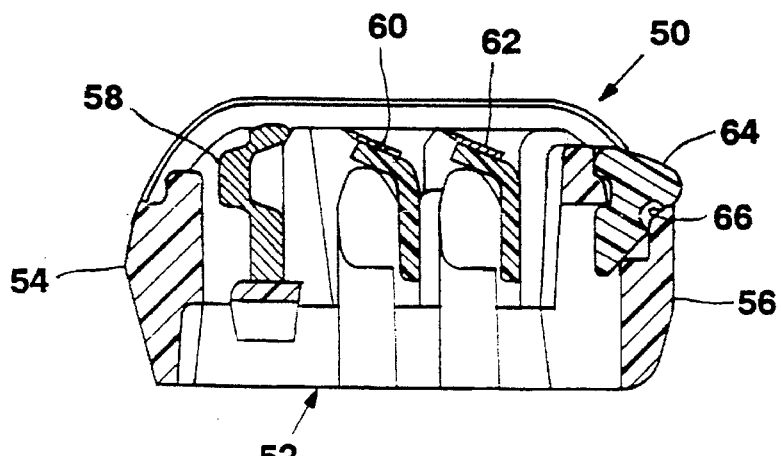
FIG. 3 is a perspective view of another razor unit in accordance with the invention.

The shaving unit 50 shown in FIG. 3 is of the type shown in Jacobson, U.S. Pat. No. 4,586,255, and includes body 52 with front portion 54 and rear portion 56. Resiliently secured in body 52 are guard member 58, leading blade unit 60 and trailing blade unit 62. A shaving aid composite in the form of elongated insert member 64 is frictionally locked in opening 66 of rear portion 56. The shaving aid composite incorporates a shaving aid which, upon contact with water, leaches out of the composite onto the skin of the user during shaving to improve the shave attributes. While shown at the rear portion of this particular shaving unit, the shaving aid composite may be located at any skin-engaging portion of the shaving unit and may be fabricated in any size or shape deemed appropriate.

The shaving aid composite of the present invention comprises an inclusion complex of a skin-soothing agent, particularly a volatile skin-soothing agent, with a cyclodextrin. Preferably the shaving aid composite comprises a matrix of a water-insoluble polymer and, dispersed within the matrix, a skin lubricating water-soluble polymer and an inclusion complex of a skin-soothing agent with a cyclodextrin. Alternatively, the shaving aid composite may comprise a sheath of water-insoluble polymer that surrounds a core which includes a skin-lubricating water-soluble polymer and an inclusion complex of a skin-soothing agent with a cyclodextrin, the sheath having a plurality of openings to facilitate release of the water-soluble polymer and skin-soothing agent. The shaving aid composite may also optionally include low molecular weight water-soluble release enhancing agents such as polyethylene glycol (e.g. 1–10% by weight), water-swellable release enhancing agents such as cross-linked polyacrylics (e.g. 2–7% by weight), colorants, antioxidants, preservatives, microbiocidal agents, beard softeners, astringents, depilatories, medicinal agents, conditioning agents, etc.

Suitable water-insoluble polymers which can be used for the matrix (or sheath) include polyethylene, polypropylene, polystyrene, butadiene-styrene copolymer (e.g. medium and high impact polystyrene), polyacetal, acrylonitrile-butadiene-styrene copolymer, ethylene vinyl acetate copolymer and blends such as polypropylene/polystyrene blend.

Preferably the water-insoluble polymer comprises about 10 to 50%, more preferably about 15 to 40%, and most preferably about 20 to 35% by weight of the shaving aid composite. The more preferred water-insoluble polymer is polystyrene, preferably a general purpose polystyrene such as Dow STYRON (Dow Chemical Company) or a high impact polystyrene (i.e. polystyrene-butadiene), such as Mobil 4324 (Mobil Corporation). The composite should contain a sufficient quantity of water-insoluble polymer to provide adequate mechanical strength, both during production and use.

Suitable skin lubricating water-soluble polymers include polyethylene oxide, polyvinyl pyrrolidone, polyacrylamide, hydroxypropyl cellulose, polyvinyl imidazoline, and polyhydroxyethylmethacrylate. Preferably the water-soluble polymer comprises about 20 to 80%, more preferably about 40 to 75%, by weight of the shaving aid composite.

The more preferred water-soluble polymers are the polyethylene oxides generally known as POLYOX (available from Union Carbide Corporation) or ALKOX (available from Meisei Chemical Works, Kyoto, Japan). These polyethylene oxides will preferably have molecular weights of about 100,000 to 6 million, most preferably about 300,000 to 5 million. The most preferred polyethylene oxide comprises a blend of about 40 to 80% of polyethylene oxide having an average molecular weight of about 5 million (e.g. POLYOX COAGULANT) and about 60 to 20% of polyethylene oxide having an average molecular weight of about 300,000 (e.g. POLYOX WSR-N-750). The polyethylene oxide blend may also advantageously contain up to about 10% by weight of a low molecular weight (i.e. MW<10,000) polyethylene glycol such as PEG-100.

The inclusion complex will generally comprise about 1% to about 25%, preferably about 5% to about 20%, most preferably about 10% to about 17%, by weight of the shaving aid composite. Any suitable cyclodextrin may be utilized to form the inclusion complex including alpha-cyclodextrin, beta-cyclodextrin, gamma-cyclodextrin and modified cyclodextrins such as hydroxypropyl-beta-cyclodextrin, methyl-beta-cyclodextrin, and acetyl-beta-cyclodextrin. The preferred cyclodextrins are beta-cyclodextrin and gamma-cyclodextrin.

Skin-soothing agents which can be used in the present invention may be any agents which have a soothing effect on the skin so as to improve shaving comfort. Particularly suitable skin-soothing agents include menthol, camphor, eugenol, eucalyptol, safrol, methyl salicylate, menthyl lactate, menthyl ethoxyacetate, menthone glycerinacetal, 3-l-menthoxypropane-1,2-diol, ethyl l-menthyl carbonate, (1S,3S,4R)-p-menth-8-en-3-ol, menthyl pyrrolidone carboxylate, N-substituted-p-menthane-3-carboxamides (as described in U.S. Pat. No. 4,136,163, which is incorporated herein by reference) including, for example, N-ethyl-p-menthane-3-carboxamide, acyclic carboxamides of the formula

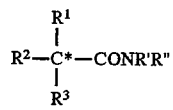

where R' and R", when taken separately, are each hydrogen, $C_1$–$C_5$ alkyl or $C_1$–$C_8$ hydroxyalkyl and provide a total of no more than 8 carbon atoms, with the proviso that when R' is hydrogen R" may also be alkylcarboxyalkyl of up to 6 carbon atoms; R' and R", when taken together, represent an alkylene group of up to 6 carbon atoms thereby forming a nitrogen heterocycle, the alkylene chain being optionally interrupted by oxygen; $R^1$ is hydrogen or $C_1$–$C_5$ alkyl; and $R^2$ and $R^3$ are each $C_1$–$C_5$ alkyl (such acyclic carboxamides being described in U.S. Pat. No. 4,153,679, which is incorporated herein by reference) including, for example, N,2,3-trimethyl-2-isopropylbutanamide, and ketal coolants (as described in WO 93/23005, which is incorporated herein by reference) including, for example, l-menthon-1d-isomenthon glycerin ketal.

The cyclodextrin inclusion complexes which are utilized in the present invention may be made in the conventional manner. Typically the cyclodextrin is dissolved in an aqueous solution at or near its solubility limit at elevated temperature. The skin-soothing agent is dispersed in this solution and the insoluble complex precipitates from the solution as it is cooled. Sufficient skin-soothing agent should be added to form a 1:1, 2:1 or 3:1 molar ratio of skin-soothing agent to cyclodextrin. The amount of skin-soothing agent which can be complexed will depend on the size of the molecule and the size of the cyclodextrin cavity. After separation of the inclusion complex, it is dried in a conventional manner, typically by oven drying (e.g. at about 100°–110° C.) optionally under vacuum. When gamma-cyclodextrin is utilized, it is also preferred to wash the complex with dry diethyl ether before drying and/or to dry it at about 116° C. overnight in order to remove all traces of water from the complex, since the presence of trace amounts of water tends to cause the skin-soothing agent to be prematurely released during fabrication of the shaving aid composites.

The shaving aid composite may additionally comprise a displacing agent which displaces the skin-soothing agent from the inclusion complex upon contact with water, thereby enhancing the release of the skin-soothing agent from the shaving aid composite during use. The displacing agent will comprise about 1% to about 10%, preferably about 2% to about 7%, most preferably about 5%, by weight of the shaving aid composite. Suitable displacing agents include surfactants, benzoic acids, and certain amines (e.g. urea).

The displacing agent is a material which is capable of forming a more stable complex with the cyclodextrin than the complex formed with the skin-soothing agent. This material will competitively displace the skin-soothing agent from the complex when the shaving aid composite is contacted with water, thus releasing the skin-soothing agent from the composite. Suitable displacing agents may be readily identified by measuring the release of skin-soothing agent (e.g. menthol) from a 0.1% aqueous solution of the inclusion complex (e.g. β-cyclodextrin/menthol) upon addition of about 0.02% of the candidate displacing agent. In this procedure the solution is evaporated in a Savant SpeedVac Concentrator (Model RT-490A), leaving a cycodextrin residue which is extracted with methanol. The methanol extract is analyzed for non-released skin-soothing agent by gas chromatography.

The following Table illustrates the displacement potential of various candidate displacing agents.

Displacement Of Menthol From 0.1% β-CD/M Complex In Water

| Displacing Agent | Menthol Released |
| --- | --- |
| Sodium lauryl sulfate | 100% |
| Sodium dodecyl benzene sulfonate | 100% |
| Disodium lauryl sulfosuccinate | 48% |
| Disodium cocamido MEA sulfosuccinate | 47% |
| Sodium diamyl sulfosuccinate | 38% |
| Cetylpyridinium chloride | 52% |
| Cetyldimethylethylammonium bromide | 50% |
| Benzalkonium chloride | 44% |
| Benzethonium chloride | 43% |
| Poloxamer 188 | 45% |
| Poloxamer 217 | 45% |
| Nonoxynol-100 | 42% |
| Poloxamer 407 | 39% |
| Poloxamer 238 | 38% |
| Laureth-23 | 36% |
| Oleth-20 | 36% |
| Benzoic acid | 46% |
| Salicylic acid | 43% |
| Urea | 61% |
| Control (β-CD/M only; no displacing agent) | 27% |

Especially preferred displacing agents include sodium lauryl sulfate, sodium dodecylbenzene sulfonate, disodium cocamido MEA sulfosuccinate (Mackanate CM-100), disodium lauryl sulfosuccinate (Mackanate LO-100), Poloxamer 188 (Pluronic F68), Poloxamer 217 (Pluronic F77), and Nonoxynol-100 (Iconol NP-100). Also preferred are benzoic acid and salicylic acid.

Shaving aid composites of the present invention may be fabricated by any appropriate method, including injection molding and extrusion, the latter being preferred. All of the components of the composite are blended prior to molding or extrusion. For best results, it is preferred that the inclusion complex is dry and has a particle size range of about 25 to 100 microns, most preferably about 40 to 75 microns. The particle size can be controlled by screening using known methods. Drying can be performed in a vacuum or convection oven at about 90°–120° C. for about 3 to 15 hours.

The blended components may be extruded through a Haake System 90 ¾ inch diameter extruder with a barrel pressure of about 1000–2000 psi, a rotor speed of about 10 to 50 rpm, and a temperature of about 150°–185° C. and a die temperature of about 170°–185° C. Alternatively, a 1 ¼ inch single screw extruder may be employed with a processing temperature of 175°–200° C., preferably 185°–190° C., a screw speed of 20 to 50 rpm, preferably 25 to 35 rpm, and an extrusion pressure of 1800 to 5000 psi, preferably 2000 to 3500 psi. The extruded strip is air cooled to about 25° C.

To injection mold the strips it is preferred to first extrude the powder blend into pellets. This can be done on a 1 ¼ or 1 ½ inch single screw extruder at a temperature of 120°–180° C., preferably 140°–150° C., with a screw speed of 20 to 100 rpm, preferably 45 to 70 rpm. The pellets are then molded in either a single material molding or multi-material molding machine, which may be single cavity or multi-cavity, optionally equipped with a hotrunner system. The process temperature can be from 165° to 250° C., preferably from 180° to 225° C. The injection pressure should be sufficient to fill the part completely without flashing. Depending on the cavity size, configuration and quantity, the injection pressure can range from 300 to 2500 psi. The cycle time is dependent on the same parameters and can range from 3 to 30 seconds, with the optimum generally being about 6 to 15 seconds.

The invention may be further illustrated by the following examples in which all parts and percentages are by weight.

EXAMPLE 1

Preparation of β-CD/M. A 10% aqueous solution of beta-cyclodextrin is prepared and maintained at 40°–45° C. with stirring. Sufficient menthol is added to provide a 1:1 molar ratio of cyclodextrin to menthol. After mixing for about three hours, the solution is allowed to cool to room temperature while maintaining continuous stirring. The precipitate is collected and dried overnight in a vacuum oven at 110° C.

EXAMPLE 2

Preparation of HP-β-CD/M. A 75% aqueous slurry of hydroxypropyl-beta-cyclodextrin is prepared and maintained at 40°–45° C. with stirring. Sufficient menthol is added to provide a 1:1 molar ratio of cyclodextrin to menthol. After mixing for about one hour, the solution is allowed to cool to room temperature while maintaining continuous stirring. The precipitate is collected by filtration and dried overnight in a vacuum oven at 110° C.

EXAMPLE 3

Preparation of γ-CD/M. Three 20% aqueous solutions of gamma-cyclodextrin are prepared and maintained at 40°–45° C. with stirring. Sufficient menthol is added to each solution to provide a 1:1, 1:2 or 1:3 molar ratio of cyclodextrin to menthol respectively. After mixing for about three hours, the solutions are allowed to cool to room temperature while maintaining continuous stirring. The precipitates are collected, dried overnight in a vacuum oven at 110° C., washed with dry diethyl ether and, after removal of the ether by water aspiration, dried in a hood. Alternatively, the collected complexes are dried in a vacuum oven at 110° C. overnight. The recovered complexes contain about 10%, about 17% and about 19% menthol respectively.

EXAMPLE 4 preparation of β-CD/menthyl lactate. A 10% aqueous solution of beta-cyclodextrin is prepared and maintained at 40°–45° C. with stirring. Sufficient menthyl lactate is added to provide a 1:1 molar ratio of cyclodextrin to menthyl lactate. After mixing for about three hours, the solution is allowed to cool to room temperature while maintaining continuous stirring. The precipitate is collected and dried overnight in a vacuum oven at 110° C.

EXAMPLE 5

Shaving aid composites similar to insert member 64 shown in FIG. 3 are fabricated from the blends indicated below by extruding the blends through a Haake System 90 ¾ inch diameter extruder with a barrel pressure of about 1000–2000 psi, a rotor speed of about 10 to 50 rpm, and a temperature of about 150°–185° C. and a die temperature of about 170°–185° C. The extruded strip of composite is cooled and sliced to appropriate lengths for securing into openings 66 of shaving units 50. In the blends listed below, the polystyrene is Dow STYRON or Mobil 2824, the high impact polystyrene ("Hips") is Mobil 4324, the polyethylene oxide (60/40) is a blend of 60% POLYOX COAGULANT (M.W. 5 million) and 40% POLYOX WSR-N-750 (M.W. 300,000), and the polyethylene glycol ("PEG") is Dow 4500 PEG (MW=4500).

| Blend A | Blend B |
|---|---|
| 28.5% Hips | 26.8% Hips |
| 46.8% polyethylene oxide | 44.0% polyethylene oxide |
| 8.5% PEG | 8.0% PEG |
| 15.0% β-CD/M | 15.0% β-CD/M |
| 1.2% colorant/antioxidant | 5.0% disodium cocamido MEA sulfosuccinate |
| | 1.2% colorant/antioxidant |

| Blend C | Blend D |
|---|---|
| 26.8% Hips | 26.8% Hips |
| 44.0% polyethylene oxide | 44.0% polyethylene oxide |
| 8.0% PEG | 8.0% PEG |
| 15.0% β-CD/M | 15.0% β-CD/M |
| 5.0% Poloxamer 188 | 5.0% sodium dodecylbenzenesulfonate |
| 1.2% colorant/antioxidant | 1.2% colorant/antioxidant |

| Blends E, F, & G | Blend H |
|---|---|
| 28.5% Hips | 28.5% Hips |
| 46.7% polyethylene oxide | 46.7% polyethylene oxide |
| 8.5% PEG | 8.5% PEG |
| 15.0% γ-CD/M (1:1, 1:2 & 1:3 resp.) | 15.0% HP-β-CD/M |
| 1.2% colorant/antioxidant | 1.2% colorant/antioxidant |

| Blend J | Blend K |
|---|---|
| 23.8% polystyrene | 26.8% Hips |
| 54.8% polyethylene oxide | 44.0% polyethylene oxide |
| 5.0% Salsorb 88 | 8.0% PEG |
| 15.0% γ-CD/M (11.4% menthol) | 15.0% β-CD/M |
| 1.4% colorant/antioxidant | 5.0% salicylic acid |
| | 1.2% colorant/antioxidant |

| Blend L | Blend M |
|---|---|
| 27.8% Hips | 33.5% Hips |
| 45.7% polyethylene oxide | 37.3% polyethylene oxide |
| 8.3% PEG | 8.0% PEG |
| 15.0% β-CD/M | 15.0% β-CD/M |
| 2.0% Na dodecylbenzenesulfonate | 5.0% disodium cocamido MEA sulfosuccinate |
| 1.2% colorant/antioxidant | 1.2% colorant/antioxidant |

| Blend N | Blend O |
|---|---|
| 26.8% Hips | 23.8% polystyrene |
| 44.0% polyethylene oxide | 49.8% polyethylene oxide |
| 8.0% PEG | 5.0% Salsorb 88 |
| 15.0% β-CD/menthyl lactate | 20.0% γ-CD/M (1:2) |
| 5.0% Nonoxynol-100 | 1.4% colorant/antioxidant |
| 1.2% colorant/antioxidant | |

| Blend P |
|---|
| 23.8% polystyrene |
| 59.8% polyethylene oxide |
| 15.0% γ-CD/M (11.4% menthol) |
| 1.4% colorant/antioxidant |

Each of the foregoing strips retains a substantial portion (i.e. >50%) of the skin-soothing agent (i.e. menthol or menthol analog) included during fabrication when stored at 45° C. for four days. In addition, each of the foregoing strips releases skin-soothing agent when contacted with water.

What is claimed is:

1. A shaving system comprising a blade member and structure defining an external skin engaging portion in proximity to said blade member, said skin engaging portion including a solid polymeric shaving aid composite comprising an inclusion complex of a skin-soothing agent with a cyclodextrin.

2. The shaving system of claim 1 wherein the shaving aid composite comprises a water-insoluble polymer, a skin lubricating water-soluble polymer, and an inclusion complex of a skin-soothing agent with a cyclodextrin.

3. The shaving system of claim 1 wherein the shaving aid composite comprises a matrix of a water-insoluble polymer and, dispersed within the matrix, a skin lubricating water-soluble polymer and an inclusion complex of a skin-soothing agent with a cyclodextrin.

4. The shaving system of claim 1, 2 or 3 wherein the cyclodextrin is selected from alpha-cyclodextrin, beta-cyclodextrin, gamma-cyclodextrin and hydroxypropyl-beta-cyclodextrin, methyl-beta-cyclodextrin, and acetyl-beta-cyclodextrin.

5. The shaving system of claim 4 wherein the skin-soothing agent is selected from the group consisting of menthol, camphor, eugenol, eucalyptol, safrol, methyl salicylate, menthyl lactate, menthyl ethoxyacetate, menthone glycerinacetal, 3-l-menthoxypropane-1,2-diol, ethyl l-menthyl carbonate, (1S,3S,4R)-p-menth-8-en-3-ol, menthyl pyrrolidone carboxylate, N-ethyl-p-menthane-3-carboxamide, N,2,3-trimethyl-2-isopropylbutanamide, and l-menthon-ld-isomenthon glycerin ketal.

6. The shaving system of claim 2 wherein the shaving aid composite additionally comprises a displacing agent which displaces the skin-soothing agent from the inclusion complex upon contact with water, thereby enhancing the release of the skin-soothing agent from the shaving aid composite during use.

7. The shaving system of claim 6 wherein the displacing agent is a surfactant.

8. The shaving system of claim 7 wherein the surfactant is selected from sodium lauryl sulfate, sodium dodecylbenzene sulfonate, disodium cocamido MEA sulfosuccinate, disodium lauryl sulfosuccinate, Poloxamer 188, Poloxamer 217 and Nonoxynol-100.

9. The shaving system of claim 6 wherein the displacing agent is benzoic acid or salicylic acid.

10. The shaving system of claim 6, 7, 8 or 9 wherein the cyclodextrin is beta-cyclodextrin.

11. The shaving system of claim 10 wherein the skin-soothing agent is selected from the group consisting of menthol, camphor, eugenol, eucalyptol, safrol, methyl salicylate, menthyl lactate, menthyl ethoxyacetate, menthone glycerinacetal, 3-l-menthoxypropane-1,2-diol, ethyl l-menthyl carbonate, (1S,3S,4R)-p-menth-8-en-3-ol, menthyl pyrrolidone carboxylate, N-ethyl-p-menthane-3-carboxamide, N,2,3-trimethyl-2-isopropylbutanamide, and l-menthon-ld-isomenthon glycerin ketal.

12. The shaving system of claim 3 wherein the shaving aid composite comprises about 15% to about 40% by weight of the water-insoluble polymer, about 20% to about 80% by weight of the water-soluble polymer, and about 1% to about 25% by weight of the inclusion complex.

13. The shaving system of claim 12 wherein the water-insoluble polymer is selected from the group consisting of polyethylene, polypropylene, polystyrene, polystyrene-butadiene copolymer, polyacetal, acrylonitrile-butadiene-styrene copolymer, and ethylene vinyl acetate copolymer and the water-soluble polymer is selected from the group consisting of polyethylene oxide, polyvinyl pyrrolidone, polyacrylamide, hydroxypropyl cellulose, polyvinyl imidazoline, and polyhydroxyethylmethacrylate.

14. The shaving system of claim 13 wherein the skin-soothing agent is selected from the group consisting of menthol, camphor, eugenol, eucalyptol, safrol, methyl salicylate, menthyl lactate, menthyl ethoxyacetate, menthone glycerinacetal, 3-l-menthoxypropane-1,2-diol, ethyl l-menthyl carbonate, (1S,3S,4R)-p-menth-8-en-3-ol, menthyl pyrrolidone carboxylate, N-ethyl-p-menthane-3-carboxamide, N,2,3-trimethyl-2-isopropyl-butanamide, and l-menthon-ld-isomenthon glycerin ketal.

15. The shaving system of claim 14 wherein the cyclodextrin is selected from alphacyclodextrin, beta-cyclodextrin, gamma-cyclodextrin and hydroxypropyl-beta-cyclodextrin, methyl-beta-cyclodextrin, and acetyl-beta-cyclodextrin.

16. The shaving system of claim 15 wherein the shaving aid composite additionally comprises about 1% to about 10% by weight of a displacing agent which displaces the skin-soothing agent from the inclusion complex upon contact with water, thereby enhancing the release of the skin-soothing agent from the shaving aid composite during use.

17. The shaving system of claim 15 or 16 wherein the shaving aid composite comprises about 20% to about 35% by weight polystyrene or polystyrene-butadiene, about 40% to about 75% by weight polyethylene oxide and about 5% to about 20% by weight inclusion complex.

18. The shaving system of claim 17 wherein the water-soluble polymer comprises a blend of polyethylene oxide having an average molecular weight of about 5 million and a polyethylene oxide having an average molecular weight of about 300,000.

19. The shaving system of claim 18 wherein the shaving aid composite additionally comprises polyethylene glycol and/or a water-swellable polymer.

* * * * *